United States Patent
Nijhawan

(10) Patent No.: US 10,568,920 B2
(45) Date of Patent: Feb. 25, 2020

(54) PHARMACEUTICAL COMPOSITIONS CONTAINING CANNABIS, USES THEREOF AND METHODS FOR IMPROVING ENERGY LEVELS AND/OR ALLEVIATING FATIGUE

(71) Applicant: Exzell Pharma Inc., Markham (CA)

(72) Inventor: Pardeep Nijhawan, Markham (CA)

(73) Assignee: Exzell Pharma Inc., Markham (CA)

(*) Notice: Subject to any disclaimer, the term of this patent is extended or adjusted under 35 U.S.C. 154(b) by 0 days.

(21) Appl. No.: 16/375,938

(22) Filed: Apr. 5, 2019

(65) Prior Publication Data

US 2019/0307826 A1    Oct. 10, 2019

(51) Int. Cl.

| | |
|---|---|
| *A61K 36/00* | (2006.01) |
| *A61K 36/185* | (2006.01) |
| *A61P 25/00* | (2006.01) |
| *A61K 31/352* | (2006.01) |
| *A61K 31/404* | (2006.01) |
| *A61K 31/714* | (2006.01) |
| *A61K 31/519* | (2006.01) |
| *A61K 31/05* | (2006.01) |
| *A61K 31/7004* | (2006.01) |

(52) U.S. Cl.
CPC ............ *A61K 36/185* (2013.01); *A61K 31/05* (2013.01); *A61K 31/352* (2013.01); *A61K 31/404* (2013.01); *A61K 31/519* (2013.01); *A61K 31/7004* (2013.01); *A61K 31/714* (2013.01); *A61P 25/00* (2018.01)

(58) Field of Classification Search
CPC ...................................................... A61K 36/00
USPC .......................................................... 424/725
See application file for complete search history.

(56) References Cited

U.S. PATENT DOCUMENTS 10,071,053 B2 *    9/2018    Victor .................... A61K 36/82

OTHER PUBLICATIONS

Cullen W, Kearney Y, Bury G. Prevalence of fatigue in general practice. Ir J Med Sci, Jan.-Mar. 2002;171(1):10-2.
Rafael de Lima Portella, Romulo Pillon Barcelos and Felix Alexandre Antunes Soares, Guarana (Paullinia cupana Kunth) effects on LDL oxidation in elderly people: an in vitro and in vivo study. Lipids Health Dis.2013;12:12.
NIH.gov Fact sheet Green Tea; U.S. Dept. of Health and Human Services; https://nccih.nih.gov/health/greentea.

* cited by examiner

*Primary Examiner* — Michael V Meller
(74) *Attorney, Agent, or Firm* — Tysver Beck Evans

(57) ABSTRACT

A pharmaceutical composition containing cannabis for increasing energy levels and/or alleviating fatigue in a patient. Also provided are a use of the pharmaceutical composition for increasing energy levels and/or alleviating fatigue in a patient, and methods for increasing energy levels and/or alleviating fatigue. The pharmaceutical composition preferably includes a combination of therapeutically effective amounts of one or more of the following medicinal ingredients: cannabis, an herb, vitamins, and/or fructose.

22 Claims, No Drawings

PHARMACEUTICAL COMPOSITIONS CONTAINING CANNABIS, USES THEREOF AND METHODS FOR IMPROVING ENERGY LEVELS AND/OR ALLEVIATING FATIGUE

FIELD OF THE INVENTION

The present invention relates to pharmaceutical compositions comprising cannabis and methods for improving energy and/or alleviating fatigue.

BACKGROUND OF THE INVENTION

There are an increasing number of patients who describe themselves as feeling fatigue often. Fatigue can be due to physical fatigue associated with excess activity or working out and mental fatigue associated with sleep deprivation, depression, boredom, jet lagged and stress. Mental fatigue does give the subjective feeling of physical fatigue. Fatigue also is commonly caused by many medical conditions such as thyroid disease, heart disease, chronic obstructive pulmonary disease (COPD), anemia, and infectious diseases such as the flu.

Many individuals do not receive treatment for fatigue as they have not had the cause of the symptoms diagnosed. The prevalence in Ireland is estimated at 25%. (See: Cullen W, Kearney Y, Bury G. Prevalence of fatigue in general practice. Ir J Med Sci, 2002 January-March; 171(1):10-2)

As common as the disorder is, the number of treatment options is limited. Usually if it is a treatable medical condition such as anemia or a limited disease state such as the flu, patients have the underlying pathology treated with time, rehydration and rest. Similarly, in situations where it is physical fatigue patients can their symptoms improved by rest, rehydration and eating a balanced diet. However, many patients who suffer from mental fatigue have a more challenging time getting relief from the symptoms of fatigue.

In addition, drugs and alcohol also are known contributors to fatigue. For example, cannabis is a drug that can cause or contribute to fatigue at higher doses and when formulated with lower levels of THC (tetrahydrocannabinol) or less than about 10 mg of THC.

What may be needed is a pharmaceutical composition of cannabis that treats low energy levels and/or fatigue while minimizing associated adverse effects.

SUMMARY OF THE INVENTION

According to an aspect of the present invention, there is disclosed a pharmaceutical composition for increasing energy level and/or alleviating fatigue in a patient while minimizing side effects. The pharmaceutical composition may preferably, but need not necessarily, comprise alone or in combination, therapeutically effective amounts of cannabis and/or herbs for use as a medicinal product prescribed by a physician, a health care practitioner or an over-the-counter product available at pharmacies, marijuana dispensaries and/or mass food stores.

According to an aspect of the invention, there is preferably disclosed a pharmaceutical composition for increasing energy level and/or alleviating fatigue in a patient while minimizing side effects. The pharmaceutical composition may preferably, but need not necessarily, additionally comprise therapeutically effective amounts of *Camellia sinesis*.

According to an aspect of the invention, there is preferably disclosed a pharmaceutical composition for increasing energy level and/or alleviating fatigue in a patient while minimizing side effects. The pharmaceutical composition may preferably, but need not necessarily, additionally comprise therapeutically effective amounts of *Paullinia cupana* (also known as guarana or Brazilian coca).

According to an aspect of the invention, there is preferably disclosed a pharmaceutical composition for increasing energy level and/or alleviating fatigue in a patient while minimizing side effects. The pharmaceutical composition may preferably, but need not necessarily, additionally comprise therapeutically effective amounts of Folate.

According to an aspect of the invention, there is preferably disclosed a pharmaceutical composition for increasing energy level and/or alleviating fatigue in a patient while minimizing side effects. The pharmaceutical composition may preferably, but need not necessarily, additionally comprise therapeutically effective amounts of Vitamin B12.

According to an aspect of the invention, there is preferably disclosed a pharmaceutical composition for increasing energy level and/or alleviating fatigue in a patient while minimizing side effects. The pharmaceutical composition may preferably, but need not necessarily, additionally comprise therapeutically effective amounts of Fructose.

According to an aspect of the invention, there is preferably disclosed a pharmaceutical composition for increasing energy level and/or alleviating fatigue in a patient while minimizing side effects. The pharmaceutical composition may preferably, but need not necessarily, comprise therapeutically effective amounts of Cannabis in any of the following form cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), a naphthoylindole, a phenylacetylindole, a benzoylindole, a cyclohexylphenole, delta-9 tetrahydrocannabinol (THC or dronabinol), delta-8 tetrahydrocannabinol (D8-THC), tetrahydrocannabinol acid (THCA), tetrahydrocannabivarin (THCV), tetrahydrocannabivarin acid (THCVA), the pharmaceutical agent is CBD, THC or a combination thereof.

According to an aspect of the invention, there is preferably disclosed a pharmaceutical composition for increasing energy levels and/or alleviating fatigue in a patient. The pharmaceutical composition may preferably, but need not necessarily, comprise a pharmaceutically acceptable excipient selected from any of the group consisting of: hydroxypropylcellulose, starch, silicon dioxide, gelatin, magnesium stearate, or microcrystalline cellulose.

According to an aspect of the invention, there is preferably disclosed a pharmaceutical composition for increasing energy levels and/or alleviating fatigue in a patient. The pharmaceutical composition may preferably, but need not necessarily, comprise the form of a tablet, caplet, capsule, dermal patch, oil drops, powder or a suspension.

Other advantages, features and characteristics of the present invention, as well as methods of use and applications of the related elements of the pharmaceutical composition and formulation will become more apparent upon consideration of the following detailed description and the appended claims, the latter of which are briefly described hereinbelow.

DETAILED DESCRIPTION OF THE PREFERRED EMBODIMENTS

The description that follows, and the embodiments described therein, is provided by way of illustration of an example, or examples, of particular embodiments of the principles and aspects of the present invention. These examples are provided for the purposes of explanation, and not of limitation, of those principles and of the invention.

It should also be appreciated that the present invention can be implemented in numerous ways, including as a use of the pharmaceutical composition or a method for increasing energy levels and/or alleviating fatigue in a patient. In this specification, these implementations, or any other form that the invention may take, may be referred to as uses or methods. In general, the order of the steps of the disclosed methods may be altered within the scope of the invention.

In this disclosure, a number of terms are used. The following definitions of such terms are provided.

As used herein, a person skilled in the relevant art may generally understand the term "comprising" to generally mean the presence of the stated features, integers, steps, or components as referred to in the claims, but that it does not preclude the presence or addition of one or more other features, integers, steps, components or groups thereof.

As used herein, the skilled reader may generally understand the term "energy" or "energetic" to generally mean to possess, exert, or display the ability to do physical work. It is the ability and strength to do active physical things and a feeling of physical power and life.

As used herein, the skilled reader may generally understand the term "fatigue" to generally mean a feeling of tiredness which is distinct from weakness and has a gradual onset. Fatigue can have physical or mental causes. Physical fatigue is the transient inability of a muscle to maintain optimal physical performance. Mental fatigue is a transient decrease in maximal cognitive performance resulting from prolonged periods of cognitive activity and can manifest as somnolence, lethargy or directed attention fatigue.

As used herein, a person skilled in the relevant art may generally understand the term "treatment" to generally refer to an approach for obtaining beneficial or desired results. Beneficial or desired results can include, but are not limited to, prevention or prophylaxis, alleviation or amelioration of one or more symptoms or conditions, diminishment of the extent of a disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a person skilled in the relevant art may generally understand the term "therapeutically effective amount" to be an amount sufficient to effect treatment when administered to a subject in need of treatment. In the case of the embodiments of the present invention, a therapeutically effective amount can include, but is not limited to, an amount for increasing energy levels and/or alleviating fatigue in a patient.

It will be understood by a person skilled in the relevant art that the compositions of the present invention can be formulated into pharmaceutical compositions for administration in a manner customary for administration of such materials using standard pharmaceutical formulation chemistries and methodologies, all of which are readily available to a person skilled in the relevant art. It will also be understood by a person skilled in the relevant art that such pharmaceutical compositions may include one or more excipients, carriers, stabilizers or other pharmaceutically inactive compounds, such as, but not limited to, wetting or emulsifying agents, pH buffering substances, hydroxypropylcellulose, starch, silicon dioxide, gelatin, magnesium stearate, microcrystalline cellulose and the like. Pharmaceutically acceptable salts can also be included therein. A thorough discussion of pharmaceutically acceptable excipients, vehicles and auxiliary substances is available in Remington's. Pharmaceutical Sciences (Mack Pub. Co. N.J. 1991). Such pharmaceutical compositions can be prepared as oral or transdermal preparations. The therapeutically effective doses may vary according to body weight and the timing and duration of administration will be determined by specific clinical research protocols.

It will be understood by a person skilled in the relevant art that the term "dose" refers to the measured quantity of an agent, preferably a therapeutic agent, to be taken at one time to have a desired therapeutic effect(s). Preferably, "dose" as used herein means a specified quantity of a pharmaceutical or therapeutic agent provided in one or more administration. It will be further understood that a "dosage unit" or "dosage form" as used herein means a form in which the active agent is provided. It will be understood that any known dosage form may be employed with the present invention. These may include, solid dosage forms, liquid dosage forms, gel dosage forms, etc. The term "effective dose" or "effective dosage" is defined as an amount sufficient to achieve or at least partially achieve the desired effect. The term "therapeutically effective dose" is defined as an amount sufficient to cure or at least partially arrest the disease and/or one or more associated symptoms in a patient already suffering from the disease.

It will be understood by a person skilled in the relevant art that the term "administering" means providing a therapeutically active agent or composition to a subject, and includes, but is not limited to, administering by a medical professional and self-administering.

It will be understood by a person skilled in the relevant art that a "pharmaceutical agent" or "therapeutic agent" as used herein means a substance that provides a therapeutic effect when administered to a subject. "Pharmaceutical composition" means a mixture of substances suitable for administering to an individual that includes one or more pharmaceutical or therapeutically effective agents. The terms "active pharmaceutical ingredient" shall be understood to refer to a substance in a pharmaceutical composition that provides a desired effect.

The treatment of low energy levels and/or fatigue in accordance with the present invention and as hereinafter defined for the purposes of this invention is directed to the improvement of energy levels and/or alleviating fatigue—including or in particularly mental fatigue—as defined herein. In a preferred embodiment of the present invention, an agent or agents which can treat low energy levels and/or fatigue is recommended. Since no pharmaceutical composition containing cannabis is presently capable of treating low energy levels and/or fatigue, a pharmaceutical composition such as is described in the present invention is recommended. Preferred embodiments of the present invention treat low energy levels and/or fatigue.

Preferably, the pharmaceutical compositions of the present invention may be provided with different active ingredients, different strengths and/or different formulations. Preferably, the pharmaceutical composition of the present invention comprises a therapeutically effective amount of cannabis. A person skilled in the relevant art would understand the term "cannabis" to refer to a genus of flowering plants in the family Cannabaceae which produce a group of chemicals called cannabinoids that produce physiological effects when administered to a patient. Persons skilled in the art will also readily appreciate that a cannabinoid is one of a class of diverse chemical compounds that acts on cannabinoid receptors (e.g., cannabinoid receptor type 1, cannabinoid receptor type 2) in cells that alter neurotransmitter release in the brain. In accordance with one or more preferred embodiments of the invention, the pharmaceutical composition may comprise cannabis-derived cannabinoids selected from the group consisting of: cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), a naphthoylindole, a phenylacetylindole, a benzoylindole, a cyclohexylphenole, delta-9 tetrahydrocannabinol (THC or dronabinol), delta-8 tetrahydrocannabinol (D8-THC), tetrahydrocannabinol acid (THCA), tetrahydrocannabivarin (THCV), tetrahydrocannabivarin acid (THCVA), the pharmaceutical agent is CBD, THC or combinations thereof. In accordance with an aspect of the present invention, compositions comprising a therapeutically effective amount of cannabis may preferably serve to increase energy level and/or alleviate fatigue in a patient. In accordance with some embodiments of the present invention, cannabis may be present in the composition in a particulate form with at least 50% by wt of the particles ranging in size from about 50 micron to about 2000 micron and wherein the particles comprise a cannabinoid, cannabinoid derivative, a terpene or a mixture thereof in a range of 1 to 30 mg of cannabinoid (CBD or THC) and most preferably from about 2.5 mg to about 10 mg per dose.

The pharmaceutical composition of the present invention may also comprise a therapeutically effective amount of one or more herbs, including but not limited to: *Camellia sinensis*; *Paullinia cupana*; and combinations thereof.

In a preferred embodiment, the pharmaceutical composition of the present invention comprises a therapeutically effective amount of *Camellia sinensis* (green tea). Persons skilled in the relevant art would understand the term "*Camellia sinensis*" to be a species of evergreen shrub or small tree whose leaves and leaf buds are used to produce tea. Persons skilled in the art will appreciate that *Camellia sinensis* has been used in Asia for medicinal purposes for thousands of years. In the prior art, it is typically consumed as a beverage and is available as a liquid extract, capsules, tablets and as topical products. It has been reported for use in cancers and heart disease to provide protective effects. *Camellia sinensis* may also act as a stimulant and can temporarily alleviate the feeling of fatigue and increase an individual's energy level. (See: NIH.gov Fact sheet Green Tea) In accordance with the present invention, compositions comprising a therapeutically effective amount of *Camelia sinensis* may preferably serve to increase energy level and/or alleviate fatigue in a patient. In accordance with some embodiments of the present invention, *Camelia sinensis* may be present in the composition from about 10 mg to about 500 mg per dose and most preferably from about 100 mg to about 200 mg per dose.

In a preferred embodiment, the pharmaceutical composition of the present invention comprises a therapeutically effective amount of *Paullinia cupana* (also known as guarana or Brazilian coca). Persons skilled in the relevant art would understand the term "*Paullinia cupana*" to be a climbing plant in the maple family, Sapindaceae, native to the Amazon basin and common to Brazil having large leaves and clusters of flowers, best known for the seeds from its fruit which are about the size of a coffee bean. Persons skilled in the art will also appreciate that *Paullinia cupana* is a seed that contains more caffeine than coffee beans and is known as a stimulant. The plant thrives in the Amazon rainforest. It has been reported to have various health benefits such as an ability to ameliorate heat stroke, cardiovascular aid, increase mental focus and acuity and some analgesic qualities. (See: Rafael de Lima Portella, Romulo Pillon Barcelos and Felix Alexandre Antunes Soares, Guarana (*Paullinia cupana Kunth*) effects on LDL oxidation in elderly people: an in vitro and in vivo study. Lipids Health Dis. 2013; 12:12) In accordance with the present invention, compositions comprising a therapeutically effective amount of *Paullinia cupana* may preferably serve to increase energy level and/or alleviate fatigue in a patient. In accordance with some embodiments of the present invention, *Paullinia cupana* may be present in the composition from about 25 mg to about 1000 mg per dose and most preferably from about 100 mg to about 200 mg per dose.

In a preferred embodiment, the pharmaceutical composition of the present invention comprises a therapeutically effective amount of folate (folic acid). A person skilled in the relevant art would understand that the term "folate" may comprise many forms of the vitamin—namely folic acid and its congeners, including tetrahydrofolic acid, methyltetrahydrofolate, methenylterahydrofolate, folinic acid, and folacin. In the prior art, folate is considered part of the B vitamins and can be found in forms such as folic acid or vitamin B9. Persons skilled in the art will also appreciate that folate is found in food and dietary supplements and is considered an essential vitamin since humans are not able to synthesize vitamin B9. Folate deficiency is known to result in anemia and can cause the feeling of being tired. Folate deficiency occurs in 1 in 10 people in the elderly patient population according to the NHS in the United Kingdom. A paper published in Neurology in 1993 by Dr. Jacobson showed that patients with chronic fatigue also had an increase incidence of Folate deficiency. Supplementing with Folate has been reported to help correct the deficiency and improve fatigue. In accordance with an aspect of the present invention, compositions comprising a therapeutically effective amount of folate may preferably serve to increase energy level and/or alleviate fatigue in a patient. In accordance with some embodiments of the present invention, folate may be present in the composition from about 25 mcg to about 2000 mcg per dose and most preferably from about 250 mcg to about 400 mcg per dose.

In a preferred embodiment, the pharmaceutical composition of the present invention comprises a therapeutically effective amount of Vitamin B12 (Cobalamin). A person skilled in the relevant art would understand that "Vitamin B12" is a coenzyme involved in the metabolism of cells of the human body, especially affecting DNA synthesis and regulation, but also fatty acid metabolism and amino acid metabolism. Persons of skill in the relevant art will also appreciate that Vitamin B12 is a water soluble vitamin that is essential for red blood cell formation, nerve function and DNA production. It is reported to be found in foods such as poultry, meat, fish and dairy products. Deficiency of Vitamin B12 is more common in vegans. Supplementation of Vitamin B12 orally or with IV infusions has been shown to correct this problem and alleviates fatigue. (See: Mayoclinic.org) In accordance with the present invention, compositions comprising a therapeutically effective amount of Vitamin B12 may preferably serve to increase energy level and/or alleviate fatigue in a patient. In accordance with some embodiments of the present invention, Vitamin B12 may be present in the composition from about 250 mcg to about 2000 mcg per dose and most preferably from about 450 mcg to about 550 mcg per dose.

In a preferred embodiment, the pharmaceutical composition of the present invention comprises a therapeutically effective amount of Fructose. A person skilled in the relevant art would understand that "Fructose" is a simple ketonic monosaccharide found in plants and is a sugar. Persons skilled in the relevant art will also understand that once ingested, the sugar is readily absorbed into the bloodstream during the digestion process, which allows the fructose molecule to enter the blood stream and make its way to the liver where it is metabolized into glucose. Skilled readers will understand that glucose is the body's primary energy source and contributes to improvement of energy levels and alleviating fatigue. In accordance with an aspect of the present invention, compositions comprising a therapeutically effective amount of Fructose may preferably serve to increase energy level and/or alleviate fatigue in a patient. In accordance with some embodiments of the present invention, Fructose may be present in the composition from about 25 mg to about 100 mg per dose and most preferably from about 30 mg to about 70 mg per dose.

In a preferred embodiment of the present invention, the combination of cannabis with herbs, vitamins and/or fructose provides advantageous outcomes as the pharmaceutical composition retains the therapeutic benefits of cannabis on relaxation to enable re-energization while minimizing its potential adverse effects.

The pharmaceutical composition may preferably, but need not necessarily, be administered in a single or multiple doses prior to bed time to increase energy levels and/or alleviate fatigue. In preferable, embodiments, a dose is taken once daily or up to four (4) times daily. In a preferred embodiment, a dosing regimen is continued until the feeling of low energy and/or fatigue has abated. In some embodiments, the composition of the present invention may be administered once daily to prevent low energy levels and/or fatigue.

In a preferred embodiment, the pharmaceutical composition of the present invention is used as a nutritional supplement to help patients who suffer from decrease energy and/or increased fatigue. The pharmaceutical composition of the present invention will preferably increase the energy level of patients and/or minimize the feeling of fatigue. Preferably, the disorders that may be treated by embodiments of the present invention include, but are not limited to, fatigue, lethargy, listless tiredness, malaise, feeling of being run down, worn out, chronic fatigue syndrome, and symptoms caused by treatable medical disorders. The pharmaceutical composition of the present invention is preferably formulated in multiple strengths to treat the symptoms associated with the above disorders. The pharmaceutical composition of the present invention is preferably formulated to use the minimal therapeutically effective doses of the active ingredients to maximize absorption in the gastrointestinal track (e.g., maximize bioavailability) and minimize side effects. In accordance with a preferred embodiment of the present invention, the pharmaceutical composition allows for a reduction in the dose of cannabis required to achieve the same therapeutic effect compared to cannabis administered to a patient in a traditional dosage form (e.g., smoking or inhalation).

In accordance with a preferred embodiment of the present invention, the pharmaceutical composition is formulated to contain cannabis comprising a higher dose of THC (delta-9-tetrahydrocannabinol) or at least 2 mg THC per dose or more preferably at least 10 mg THC per dose. An advantage of such formulations is to prevent the onset of, or contribution to, cannabis-induced fatigue which has been reported to occur with higher doses of cannabis.

In accordance with a preferred embodiment of the present invention, the administration of lower doses of cannabis (compared to cannabis administered in a traditional dosage form, for example, smoking or inhalation) combined with the herbs, vitamins and fructose disclosed herein is advantageous as it provides a therapeutic effect on improving energy levels and/or alleviating fatigue and a reduction in cravings for further cannabis that chronic cannabis users may experience.

In accordance with a preferred embodiment of the present invention, the combination of cannabis, herbs, vitamins and/or fructose disclosed herein is advantageous as it may provide an unexpected synergistic therapeutic effect on improving energy levels and/or alleviating fatigue.

In accordance with a preferred embodiment of the present invention, the combination of cannabis, herbs, vitamins and/or fructose disclosed herein is advantageous as it may unexpectedly allow for the use of a lower dose of cannabis to achieve a similar therapeutic effect when compared to cannabis administered to a patient in a traditional dosage form (e.g., smoking or inhalation).

In accordance with a preferred embodiment of the present invention, the combination of cannabis, herbs, vitamins and/or fructose disclosed herein is advantageous as it may allow for the use of a lower dose of cannabis to reduce the severity and/or number of potential cannabis-related adverse effects.

The pharmaceutical composition of the present invention is a formulation comprising cannabis in addition to various herbs, vitamins and fructose, either used as a medicine prescribed by a physician, a health care practitioner, or an over-the-counter product available in pharmacies, marijuana dispensaries, and mass food stores and will preferably help patients who suffer from sleeping disorders achieve more energy.

In accordance with a preferred embodiment of the present invention, the pharmaceutical composition comprising cannabis, herbs, vitamins and fructose may be administered once or up to four (4) times daily prior to bedtime during periods of low energy and/or fatigue. The pharmaceutical composition of the present invention delivers high concentrations of several herbs and vitamins including *Camellia sinensis, Paullinia cupana*, Folate, Vitamin B12 (cobalamin), fructose and therapeutically effective concentrations of cannabis in any form without causing increased side effects. The combination of the foregoing herbs, vitamins, fructose and cannabis in a single formulation to increase energy level and/or alleviate fatigue in a patient is unique and has not been previously described.

Persons skilled in the relevant art may find it counterintuitive to find that cannabis may improve energy levels when it has been reported to cause sleepiness. In accordance with preferred embodiments of the present invention, however, cannabis administered in predetermined doses in combination with the supplements described herein allows for the body to relax and be re-energized. The pharmaceutical composition of the present invention is formulated to provide seemingly paradoxical effects as the predetermined therapeutically effective dose of cannabis provides patients with an increase in energy level.

Example 1

The following example sets out a preferred formulation of the pharmaceutical composition in accordance with the present invention to increase energy level and/or alleviate fatigue in a patient.

| Medicinal Ingredients | Quantity |
| --- | --- |
| *Camellia sinensis* | 156.5 mg |
| Folate | 300.0 mcg |
| Fructose | 50.0 mg |
| *Paullinia cupana* | 170.4 mg |
| Vitamin B12 | 500.0 mcg |
| Cannabis (THC) | 0.05 g to 2 g of 10% to 50% THC levels |

In preferred embodiments of the invention, the formulation is allergen free (e.g., egg products, wheat (gluten) and dairy (lactose)). In addition, all compounds in the formulation are preferably gluten free.

Example 2

Background:

A test formulation comprising a combination of *Camellia sinensis* (156.5 mg), folate (300.0 mcg), Fructose (50.0 mg), *Paullinia cupana* (170.4 mg), Vitamin B12 (500.0 mcg), and Cannabis (THC) (0.05 g to 2 g of 10% to 50% THC levels) was prepared in a capsule dosage form to study the effectiveness of the combination on increasing energy level and/or alleviating fatigue in a patient.

Objective:

To assess whether the test formulation described above is effective in the increase of energy level and/or reduction of fatigue in a patient.

Methods:

A 30 year old male experiences anxiety and suffers from decreased energy. The subject was administered the capsule formulation twice daily for two weeks and then qualitatively assessed for energy level and fatigue.

Results:

The subject experienced greater energy levels and lower anxiety and fatigue. No obvious adverse effects of the test formulation were identified.

CONCLUSIONS

The test formulation may be effective to increase energy levels and/or alleviate fatigue in a patient. Further studies may be needed to qualitatively and/or quantitatively assess improvement in energy levels and reduction in fatigue and to determine the preferred medicinal ingredients (including the preferred quantity of each) to include in the composition as well as the potential adverse effects associated with same.

The above description is meant to be exemplary only, and one skilled in the art will recognize that changes may be made to the embodiments described without departing from the scope of the invention disclosed. Modifications which fall within the scope of the scope of the present invention will be apparent to those skilled in the art, in light of a review of this disclosure, and such modifications are intended to fall within the appended claims.

This concludes the description of presently preferred embodiments of the invention. The foregoing description has been presented for the purpose of illustration and is not intended to be exhaustive or to limit the invention to the precise form disclosed. Other modification, variations and alterations are possible in light of the above teaching and will be apparent to those skilled in the art, and may be used in the design and manufacture of other embodiments according to the present invention without departing from the spirit and scope of the invention. It is intended the scope of the invention be limited not by this description but only by the claims forming a part hereof.

What is claimed is:

1. A tablet, caplet, capsule or dermal patch consisting essentially of a cannabis extract, a *Camellia sinensis* extract, and a *Paullinia cupana* extract.

2. The tablet, caplet, capsule or dermal patch of claim 1 wherein the tablet, caplet, capsule or dermal patch consists essentially of from about 10 mg to about 500 mg of the *Camellia sinesis* extract per dose and from about 25 mg to about 1000 mg of the *Paullinia cupana* extract per dose.

3. The tablet, caplet, capsule or dermal patch of claim 1 wherein the tablet, caplet, capsule or dermal patch consists essentially of from about 100 mg to about 200 mg of the *Camellia sinesis* extract per dose and from about 100 mg to about 200 mg of the *Paullinia cupana* extract per dose.

4. The tablet, caplet, capsule or dermal patch of claim 1 wherein the tablet, caplet, capsule or dermal patch consists essentially of from about 10 mg to about 500 mg of the *Camellia sinesis* extract per dose.

5. The tablet, caplet, capsule or dermal patch of claim 1 wherein the tablet, caplet, capsule or dermal patch consists essentially of from about 25 mg to about 1000 mg of the *Paullinia cupana* extract per dose.

6. The tablet, caplet, capsule or dermal patch of claim 1 wherein the tablet, caplet, capsule or dermal patch consists essentially of from about 1 mg to about 30 mg of the cannabis extract per dose.

7. The tablet, caplet, capsule or dermal patch of claim 1 wherein the tablet, caplet, capsule or dermal patch consists essentially of from about 2.5 mg to about 10 mg of the cannabis extract per dose.

8. The tablet, caplet, capsule or dermal patch of claim 1 further consisting essentially of fructose.

9. The tablet, caplet, capsule or dermal patch of claim 8 wherein the tablet, caplet, capsule or dermal patch consists essentially of from about 25 mg to about 100 mg of the fructose per dose.

10. The tablet, caplet, capsule or dermal patch of claim 8 wherein the tablet, caplet, capsule or dermal patch consists essentially of from about 30 mg to about 70 mg of the fructose per dose.

11. A tablet, caplet, capsule or dermal patch consisting essentially of a cannabis extract, a *Camellia sinensis* extract, a *Paullinia cupana* extract and a vitamin selected from the group consisting of: Vitamin B9; Vitamin B12; and combinations thereof.

12. The tablet, caplet, capsule or dermal patch of claim 11 wherein the tablet, caplet, capsule or dermal patch consists essentially of from about 10 mg to about 500 mg of the *Camellia sinesis* extract per dose and from about 25 mg to about 1000 mg of the *Paullinia cupana* extract per dose.

13. The tablet, caplet, capsule or dermal patch of claim 11 wherein the tablet, caplet, capsule or dermal patch consists essentially of from about 100 mg to about 200 mg of the *Camellia sinesis* extract per dose and from about 100 mg to about 200 mg of the *Paullinia cupana* extract per dose.

14. The tablet, caplet, capsule or dermal patch of claim 11 wherein the tablet, caplet, capsule or dermal patch consists essentially of from about 10 mg to about 500 mg of the *Camellia sinesis* extract per dose.

15. The tablet, caplet, capsule or dermal patch of claim 11 wherein the tablet, caplet, capsule or dermal patch consists essentially of from about 25 mg to about 1000 mg of the *Paullinia cupana* extract per dose.

16. The tablet, caplet, capsule or dermal patch of claim 11 wherein the tablet, caplet, capsule or dermal patch consists essentially of from about 1 mg to about 30 mg of the cannabis extract per dose.

17. The tablet, caplet, capsule or dermal patch of claim 11 wherein the tablet, caplet, capsule or dermal patch consists essentially of from about 2.5 mg to about 10 mg of the cannabis extract per dose.

18. The tablet, caplet, capsule or dermal patch of claim 11 wherein the tablet, caplet, capsule or dermal patch consists essentially of from about 25 mcg to about 2000 mcg of Vitamin B9 per dose and from about 250 mcg to about 2000 mcg of Vitamin B12 per dose.

19. The tablet, caplet, capsule or dermal patch of claim 11 wherein the tablet, caplet, capsule or dermal patch consists essentially of from about 250 mcg to about 400 mcg of Vitamin B9 per dose and from about 450 mcg to about 550 mcg of Vitamin B12 per dose.

20. The caplet, capsule or dermal patch of claim 11 further consisting essentially of fructose.

21. The tablet, caplet, capsule or dermal patch of claim 20 wherein the tablet, caplet, capsule or dermal patch consists essentially of from about 25 mg to about 100 mg of the fructose per dose.

22. The tablet, caplet, capsule or dermal patch of claim 20 wherein the tablet, caplet, capsule or dermal patch consists essentially of from about 30 mg to about 70 mg of the fructose per dose.

* * * * *

UNITED STATES PATENT AND TRADEMARK OFFICE
CERTIFICATE OF CORRECTION

PATENT NO. : 10,568,920 B2
APPLICATION NO. : 16/375938
DATED : February 25, 2020
INVENTOR(S) : Pradeep Nijhawan Page 1 of 1

It is certified that error appears in the above-identified patent and that said Letters Patent is hereby corrected as shown below:

On the Title Page

Item (30), should read:
Foreign Application Priority Data
April 6, 2018    (CA).....................3000495

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*